United States Patent
Yamada et al.

(10) Patent No.: US 9,594,049 B2
(45) Date of Patent: Mar. 14, 2017

(54) GAS SENSOR CONTROL APPARATUS (71) Applicant: DENSO CORPORATION, Kariya, Aichi-pref. (JP)

(72) Inventors: Yuji Yamada, Nagoya (JP); Mikiyasu Matsuoka, Obu (JP); Takamasa Oguri, Toyoake (JP); Takao Mishima, Kariya (JP)

(73) Assignee: DENSO CORPORATION, Kariya (JP)

( * ) Notice: Subject to any disclaimer, the term of this patent is extended or adjusted under 35 U.S.C. 154(b) by 237 days.

(21) Appl. No.: 14/455,089

(22) Filed: Aug. 8, 2014

(65) Prior Publication Data
US 2015/0041320 A1  Feb. 12, 2015

(30) Foreign Application Priority Data

Aug. 9, 2013  (JP) .................. 2013-167127

(51) Int. Cl.
*G01N 27/407* (2006.01)
*F01N 11/00* (2006.01)
(Continued)

(52) U.S. Cl.
CPC ......... *G01N 27/407* (2013.01); *F01N 11/007* (2013.01); *F02D 41/1495* (2013.01); *G01N 27/4065* (2013.01); *F01N 3/101* (2013.01); *F01N 2560/025* (2013.01); *F01N 2560/14* (2013.01); *F01N 2900/0416* (2013.01);
(Continued)

(58) Field of Classification Search
None
See application file for complete search history.

(56) References Cited

U.S. PATENT DOCUMENTS 4,716,760 A   1/1988  Osuga et al.
4,762,604 A   8/1988  Asakura et al.
(Continued)

FOREIGN PATENT DOCUMENTS

JP   2013-177884 A   9/2013

OTHER PUBLICATIONS

Japanese Office Action mailed on Jul. 14, 2015 in the corresponding JP application No. 2013-167127. ( English translation attached.).
(Continued)

*Primary Examiner* — Matthew Martin
*Assistant Examiner* — Steven E Rosenwald
(74) *Attorney, Agent, or Firm* — Posz Law Group, PLC (57) ABSTRACT An $O_2$ sensor has a sensor element, which includes a solid electrolyte layer and a pair of electrodes. The solid electrolyte layer is held between the electrodes, which includes an atmosphere side electrode and an exhaust side electrode. A constant current circuit is installed in an electric path, which connects between the atmosphere side electrode and a ground, to induce a flow of a predetermined constant electric current between the electrodes through the solid electrolyte layer. A voltage circuit is installed in an electric path, which connects between the exhaust side electrode and a ground, to increase an electric potential of the exhaust side electrode by a predetermined amount relative to an electric potential at an output side of the constant current circuit, from which the electric current flows out of the constant current circuit.

5 Claims, 8 Drawing Sheets (51) Int. Cl.
*G01N 27/406* (2006.01)
*F02D 41/14* (2006.01)
*F01N 3/10* (2006.01)

(52) U.S. Cl.
CPC ............... *F01N 2900/1402* (2013.01); *F01N 2900/1621* (2013.01); *F02D 41/1454* (2013.01); *Y02T 10/22* (2013.01); *Y02T 10/47* (2013.01)

(56) References Cited

U.S. PATENT DOCUMENTS

| | | | |
|---|---|---|---|
| 5,298,865 A | 3/1994 | Denz et al. | |
| 2004/0100271 A1* | 5/2004 | Ikeda | G01N 33/007 324/514 |
| 2012/0043205 A1* | 2/2012 | Matsuoka | G01N 27/407 204/410 |

OTHER PUBLICATIONS

U.S. Appl. No. 14/455,051, filed Aug. 8, 2014, Yamada et al.
U.S. Appl. No. 14/454,769, filed Aug. 8, 2014, Yamada et al.
U.S. Appl. No. 14/454,792, filed Aug. 8, 2014, Matsuoka et al.

* cited by examiner

GAS SENSOR CONTROL APPARATUS

CROSS REFERENCE TO RELATED APPLICATION

This application is based on and incorporates herein by reference Japanese Patent Application No. 2013.167127 filed on Aug. 9, 2013.

TECHNICAL FIELD

The present invention relates to a gas sensor control apparatus.

BACKGROUND

For instance, a gas sensor, which outputs an electromotive force, is provided at a vehicle engine (e.g., an automobile engine). In this type of gas sensor, exhaust gas, which is discharged from the engine, serves as a sensing subject of the gas sensor, and an oxygen concentration of the exhaust gas is sensed with the gas sensor. This type of gas sensor includes an electromotive force (EMF) cell, which outputs an electromotive force signal that varies depending on whether the exhaust gas is rich or lean. Specifically, when an air-to-fuel ratio is rich, the electromotive force cell outputs the electromotive force signal of about 0.9 V. In contrast, when the air-to-fuel ratio is lean, the electromotive force cell outputs the electromotive force signal of about 0 V.

In this type of gas sensor, when the air-to-fuel ratio of the exhaust gas changes between rich and lean, a change in the sensor output may be disadvantageously delayed relative to an actual change in the air-to-fuel ratio. In order to improve the output characteristic of such a gas sensor, various techniques have been proposed.

For instance, JP2012-063345A (corresponding to US2012/0043205A1) discloses a gas sensor control apparatus, in which a constant current circuit is connected to at least one of a pair of sensor electrodes (i.e., two sensor electrodes). In this gas sensor control apparatus, when it is determined that a demand for changing the output characteristic of the gas sensor is present, a flow direction of the constant electric current is determined based on the demand. Then, the constant current circuit is controlled to supply the constant electric current in the determined direction. Specifically, the constant current circuit can supply the constant electric current in any one of a forward direction and a backward direction and can adjust a current value of the electric current through a pulse width modulation (PWM) control operation.

However, in the above-describe technique, the supply of the constant electric current of the constant current circuit is controlled through the PWM control operation. In order to meet, for example, a cost reduction demand, an improvement may be made to simplify the structure.

In order to simplify the structure of the constant current circuit, the electromotive force cell, which is in the electromotive force generating state, is used as a battery, and a flow of an electric current may be induced in the electromotive force cell through use of the electromotive force generated by the electromotive force cell. However, in the case where the electromotive force of the electromotive force cell is used to induce the flow of the electric current in the electromotive force cell, the flow of the constant electric current, which is conducted through the electromotive force cell, is influenced by the voltage value of the electromotive force. In a state where the electromotive force of the electromotive force cell is relatively small, the current value of the constant electric current may possibly be excessively reduced to have an unexpectedly small value. That is, in the case of the electromotive force cell of the gas sensor, the voltage value of electromotive force cell changes in the range of 0 to 0.9 V. In the lean state, the current value of the constant electric current may possibly become the excessively small value, or the constant electric current cannot be conducted through the electromotive force cell. Therefore, there is a need for improvement.

SUMMARY

The present disclosure is made in view of the above disadvantage.

According to the present disclosure, there is provided a gas sensor control apparatus for a gas sensor that outputs an electromotive force signal corresponding to an air-to-fuel ratio of an exhaust gas of an internal combustion engine and includes an electromotive force cell, which has a solid electrolyte body and a pair of electrodes. The solid electrolyte body is held between the pair of electrodes that include a reference side electrode, which becomes a positive side at a time of outputting an electromotive force from the electromotive force cell, and an exhaust side electrode, which becomes a negative side at the time of outputting the electromotive force from the electromotive force cell. The gas sensor control apparatus includes a current conduction regulating device and a voltage circuit. The current conduction regulating device is installed in an electric path, which is connected to the electromotive force cell, to induce a flow of an electric current between the exhaust side electrode and the reference side electrode through the solid electrolyte body in the electromotive force cell while using the electromotive force of the electromotive force cell as an electric power source. The voltage circuit increases an electric potential of the exhaust side electrode by a predetermined amount relative to an electric potential at an output side of the current conduction regulating device, from which the electric current flows out of the current conduction regulating device.

BRIEF DESCRIPTION OF THE DRAWINGS

The drawings described herein are for illustration purposes only and are not intended to limit the scope of the present disclosure in any way.

DETAILED DESCRIPTION

Figure 1:
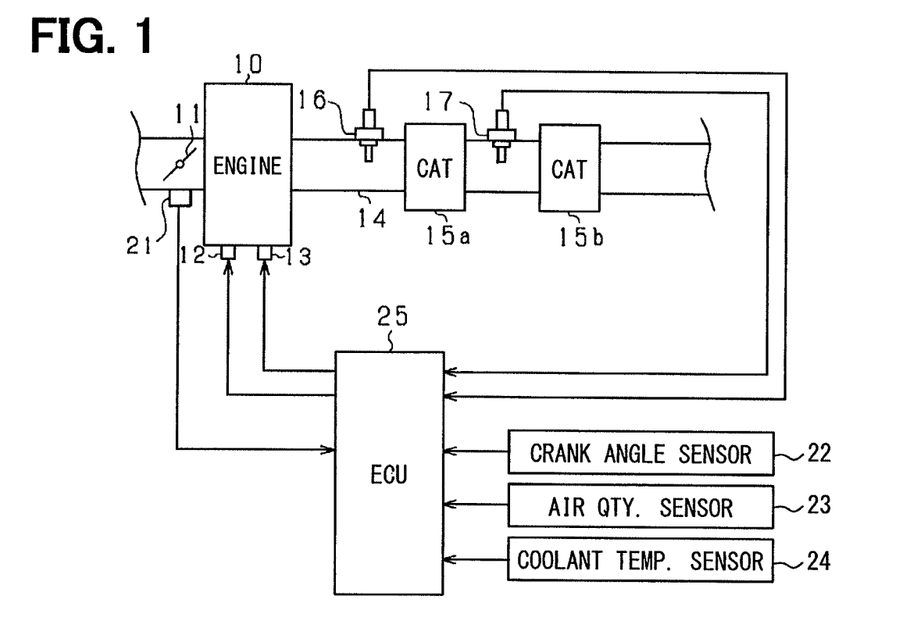
FIG. 1 is a diagram schematically showing an entire structure of an engine control system according to an embodiment of the present disclosure.

An embodiment of the present disclosure will be described with reference to the accompanying drawings. In the present embodiment, a gas sensor, which is provided in an exhaust conduit of an engine (internal combustion engine) of a vehicle (e.g., an automobile), is used, and there will be described an engine control system, which executes various control operations of the engine based on an output of the gas sensor. In the engine control system, an electronic control unit (hereinafter referred to as an ECU) is used to execute, for example, a control operation of a fuel injection quantity and a control operation of ignition timing. FIG. 1 is a diagram that schematically shows an entire structure of the engine control system.

In FIG. 1, the engine 10 is, for example, a gasoline engine and has an electronically controlled throttle valve 11, fuel injection valves 12, and ignition devices 13. Catalysts (also referred to as catalytic converters) 15a, 15b, which serve as an exhaust gas purifying device, are installed in an exhaust conduit 14 (serving as an exhaust device) of the engine 10. Each of the catalysts 15a, 15b is formed as, for example, a three-way catalyst. The catalyst 15a is a first catalyst, which serves as an upstream side catalyst, and the catalyst 15b is a second catalyst, which serves as a downstream side catalyst. As is well known in the art, the three-way catalyst purifies three noxious components of the exhaust gas, i.e., CO (carbon monoxide), HC (hydrocarbon) and NOx (nitrogen oxide, such as NO) and is formed by applying metal, such as platinum, palladium, rhodium, to a ceramic substrate that is configured into, for example, a honeycomb form or a lattice form. In this instance, at the three-way catalyst, CO and HC, which are the rich components, are purified through an oxidation reaction, and NOx, which is the lean component, is purified through a reduction reaction.

An air-to-fuel ratio (A/F) sensor 16 is placed on an upstream side of the first catalyst 15a in a flow direction of the exhaust gas, and an oxygen (02) sensor 17 is placed between the first catalyst 15a and the second catalyst 15b, i.e., is placed on the downstream side of the first catalyst 15a and on the upstream side of the second catalyst 15b in the flow direction of the exhaust gas. The A/F sensor 16 outputs an A/F signal, which is generally proportional to the air-to-fuel ratio of the exhaust gas. Furthermore, the $O_2$ sensor 17 outputs an electromotive force (EMF) signal, which varies depending on whether the air-to-fuel ratio of the exhaust gas is rich or lean.

Furthermore, various sensors, such as a throttle opening degree sensor 21, a crank angle sensor 22, an air quantity sensor 23 and a coolant temperature sensor 24, are installed in the engine control system. The throttle opening degree sensor 21 senses the opening degree of the throttle valve 11. The crank angle sensor 22 outputs a crank angle signal of a rectangular waveform at every predetermined crank angle (e.g., a period of 30 degree crank angle) of the engine 10. The air quantity sensor 23 senses the quantity of the intake air drawn into the engine 10. The coolant temperature sensor 24 senses the temperature of the engine coolant. Although not depicted in the drawings, besides the above sensors, there are also provided, for example, a combustion pressure sensor, which senses a combustion pressure in a cylinder of the engine, an accelerator opening degree sensor, which senses an opening degree of an accelerator (an accelerator manipulation amount or an amount of depression of an accelerator pedal), and an oil temperature sensor, which senses a temperature of an engine lubricating oil. These sensors respectively serve as an operational state sensing means.

The ECU 25 includes a microcomputer of a known type, which has a CPU, a ROM, and a RAM (memories). The ECU 25 executes various control programs, which are stored in the ROM, to perform various control operations of the engine 10 according to the engine operational state. Specifically, the ECU 25 receives signals from the above-described sensors, and the ECU 25 computes each corresponding fuel injection quantity and each corresponding ignition timing to execute, for example, the control operation for driving the fuel injection valves 12 and the control operation for driving the ignition devices 13 based on the signals.

Particularly, with respect to the fuel injection quantity control operation, the ECU 25 performs an air-to-fuel ratio feedback control operation based on a measurement signal of the NF sensor 16, which is placed on the upstream side of the first catalyst 15a, and a measurement signal of the $O_2$ sensor 17, which is placed on the downstream side of the first catalyst 15a. Specifically, the ECU 25 executes a main feedback control operation in such a manner that an actual air-to-fuel ratio (an actual air-to-fuel ratio at the location on the upstream side of the first catalyst 15a), which is sensed with the A/F sensor 16, coincides with a target air-to-fuel ratio, which is set based on the engine operational state. Also, the ECU 25 executes a sub-feedback control operation in such a manner that an actual air-to-fuel ratio (an actual air-to-fuel ratio at the location on the downstream side of the first catalyst 15a), which is sensed with the $O_2$ sensor 17, coincides with the target air-to-fuel ratio. In the sub-feedback control operation, in view of, for example, a difference between the actual air-to-fuel ratio on the downstream side of the first catalyst 15a and the target air-to-fuel ratio, the target air-to-fuel ratio used in the main feedback control operation is corrected, or a feedback correction amount used in the main feedback control operation is corrected. The ECU 25 executes a stoichiometric feedback control operation, which sets the target air-to-fuel ratio to a stoichiometric air-to-fuel ratio, as the air-to-fuel ratio control operation.

Figure 2:
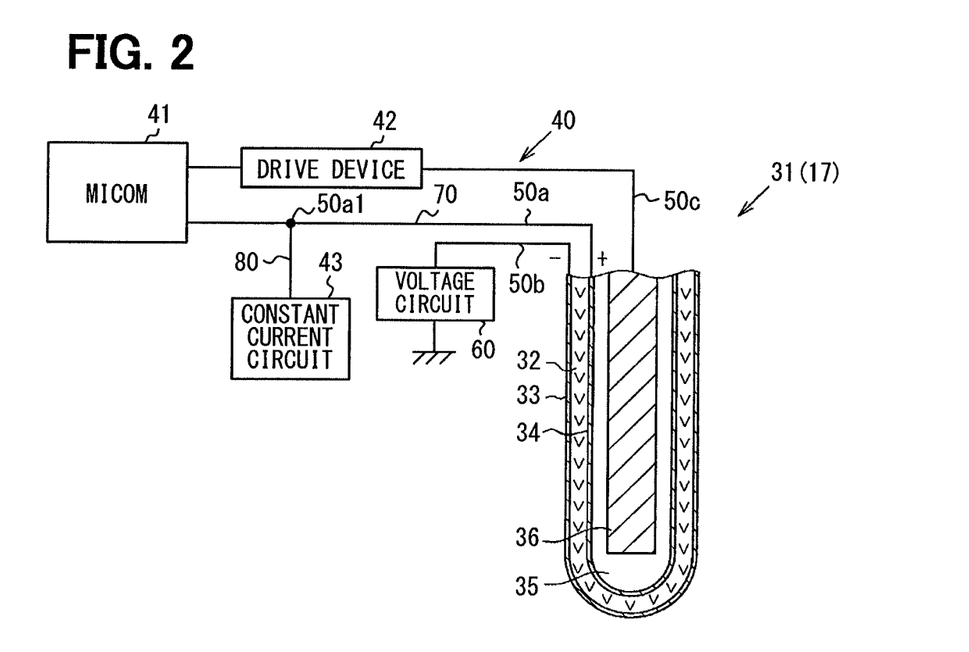
FIG. 2 is a diagram schematically showing a cross section of a sensor element and a sensor control arrangement of the embodiment.

Next, the structure of the $O_2$ sensor 17, which is placed on the downstream side of the first catalyst 15a, will be described. The $O_2$ sensor 17 has a sensor element (also referred to as a sensing device) 31, which is configured into a cup shape. FIG. 2 shows a cross section of the sensor element 31. In reality, the sensor element 31 is configured such that the entire sensor element 31 is received in a housing or an element cover, and the sensor element 31 is placed in the engine exhaust conduit 14. The sensor element 31 serves as an electromotive force cell.

In the sensor element 31, a solid electrolyte layer (serving as a solid electrolyte body) 32 has a cup shaped cross section. An exhaust side electrode 33 is formed in an outer surface of the solid electrolyte layer 32, and an atmosphere side electrode 34 is formed in an inner surface of the solid electrolyte layer 32. Each of the electrodes 33, 34 is formed as a layer on the corresponding one of the outer surface and the inner surface of the solid electrolyte layer 32. The solid electrolyte layer 32 is an oxide sintered body, which conducts oxygen ions therethrough and is formed by completely dissolving CaO, MgO, Y2O3, and/or Yb2O3 as stabilizer into ZrO2, HfO2, ThO2, and/or Bi2O3. Furthermore, each electrode 33, 34 is made of a noble metal, such as platinum, which has the high catalytic activity, and a surface of the electrode 33, 34 is covered with a porous coating that is chemically plated. The above-described two electrodes 33, 34 serve as a pair of electrodes (sensor electrodes). An inside space, which is surrounded by the solid electrolyte layer 32, is an atmosphere chamber (a reference gas chamber or simply referred to as a reference chamber) 35. A heater 36 is received in the atmosphere chamber 35. The heater 36 has a sufficient heat capacity to activate the sensor element 31, and the sensor element 31 is entirely heated by a heat energy, which is generated from the heater 36. An activation temperature of the $O_2$ sensor 17 is, for example, 500 to 650 degrees Celsius. The atmosphere gas (atmosphere air) is introduced into the atmosphere chamber 35, so that the inside of the atmosphere chamber 35 is maintained at a predetermined oxygen concentration.

In the sensor element 31, the exhaust gas is present at the outside (the electrode 33 side) of the solid electrolyte layer 32, and the atmosphere gas (atmosphere air) is present at the inside (the electrode 34 side) of the solid electrolyte layer 32. An electromotive force is generated between the electrode 33 and the electrode 34 in response to a difference in an oxygen concentration (a difference in an oxygen partial pressure) between the outside (the electrode 33 side) of the solid electrolyte layer 32 and the inside (the electrode 34 side) of the solid electrolyte layer 32. Specifically, the generated electromotive force varies depending on whether the air-to-fuel ratio is rich or lean. In such a case, the oxygen concentration at the exhaust side electrode 33 is lower than the oxygen concentration at the atmosphere side electrode 34, which serves as a reference side electrode, and the electromotive force is generated at the sensor element 31 while the atmosphere side electrode 34 and the exhaust side electrode 33 serve as a positive side and a negative side, respectively. In this instance, the exhaust side electrode 33 is grounded through an electric path 50b, as shown in FIG. 2. Thus, the $O_2$ sensor 17 outputs the electromotive force signal, which corresponds to the oxygen concentration (the air-to-fuel ratio) of the exhaust gas.

Figure 3:
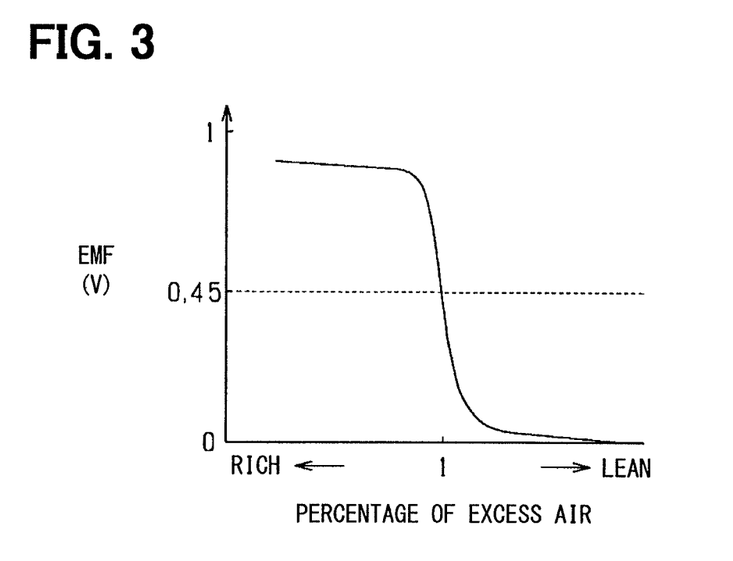
FIG. 3 is an electromotive force characteristic diagram indicating a relationship between an air-to-fuel ratio and an electromotive force of the sensor element.

FIG. 3 is an electromotive force characteristic diagram showing a relationship between the air-to-fuel ratio of the exhaust gas and the electromotive force of the sensor element 31. In FIG. 3, the axis of abscissas indicates a percentage of excess air λ. When the percentage of excess air λ is 1 (i.e., λ=1), the air-to-fuel ratio is the stoichiometric air-to-fuel ratio (stoichiometric mixture), which is also referred to as a theoretical air-to-fuel ratio. The sensor element 31 has the characteristics of that the electromotive force generated from the sensor element 31 varies depending on whether the air-to-fuel ratio is rich or lean, and the electromotive force generated from the sensor element 31 rapidly changes around the stoichiometric air-to-fuel ratio. Specifically, the electromotive force (also referred to as a sensor electromotive force) of the sensor element 31 at the rich time is about 0.9 V, and the electromotive force of the sensor element 31 at the lean time is about 0 V.

In FIG. 2, a sensor control arrangement (also referred to as a sensor control apparatus) 40 is connected to the sensor element 31. When the electromotive force is generated at the sensor element 31 in response to the air-to-fuel ratio (the oxygen concentration) of the exhaust gas, the sensor measurement signal (the electromotive force signal), which corresponds to the electromotive force generated at the sensor element 31, is outputted from the sensor element 31 to a microcomputer 41 of the sensor control arrangement 40 through an electric path 50a. The microcomputer 41 has a CPU, a ROM, and a RAM (memories), and executes various operations upon execution of each corresponding program stored in one or more of the memories. The microcomputer 41 computes the air-to-fuel ratio based on the electromotive force signal of the sensor element 31. The sensor control arrangement 40 is formed in the ECU 25 of FIG. 1. At the ECU 25, the microcomputer 41 is formed as a computing device (computing means) that has an engine control function and a sensor control function. In this case, the microcomputer 41 computes the engine rotational speed and the intake air quantity based on the measurement results of the various sensors. However, instead of having the single microcomputer, the ECU 25 may be constructed to have an engine control microcomputer, which executes the engine control function, and a sensor control microcomputer, which executes the sensor control function, if desired.

Furthermore, the microcomputer 41 determines an activated state of the sensor element 31 and controls the driving operation of the heater 36 through a drive device 42, which is connected to the heater 36 through an electric path 50c, based on a result of determination of the activated state of the sensor element 31. The technique of the activation determination of the sensor element 31 and the technique of the heater control are already known. Therefore, the activation determination of the sensor element 31 and the heater control will be briefly described. The microcomputer 41 periodically changes the voltage or the electric current applied to the sensor element 31 in a manner that is similar to an alternating current and senses a thus generated change in the electric current or a thus generated change in the electric voltage. A resistance of the sensor element 31 (an impedance of the sensor element 31) is computed based on the change in the electric current or the change in the voltage, and the energization control operation of the heater 36 is executed based on the resistance of the sensor element 31. At that time, there is a correlation between the activated state of the sensor element 31 (the temperature of the sensor element 31) and the resistance of the sensor element 31. When the resistance of the sensor element 31 is controlled to a predetermined target value, the sensor element 31 is held in the desired activated state (the state, under which the activation temperature of the sensor element 31 is held in a range of 500 to 650 degrees Celsius). For example, a sensor element temperature feedback control operation may be executed as the heater control operation.

When the engine 10 is operated, the actual air-to-fuel ratio of the exhaust gas is changed. For example, the air-to-fuel ratio may be repeatedly changed between rich and lean. At the time of changing the actual air-to-fuel ratio between rich and lean, when a deviation exists between the output of the $O_2$ sensor 17 and the presence of NOx, which is the lean component, the emission performance may possibly be influenced. For example, the amount of NOx in the exhaust gas may possibly be increased beyond the intended amount at the time of operating the engine 10 under the high load (the time of accelerating the vehicle).

Figure 4:
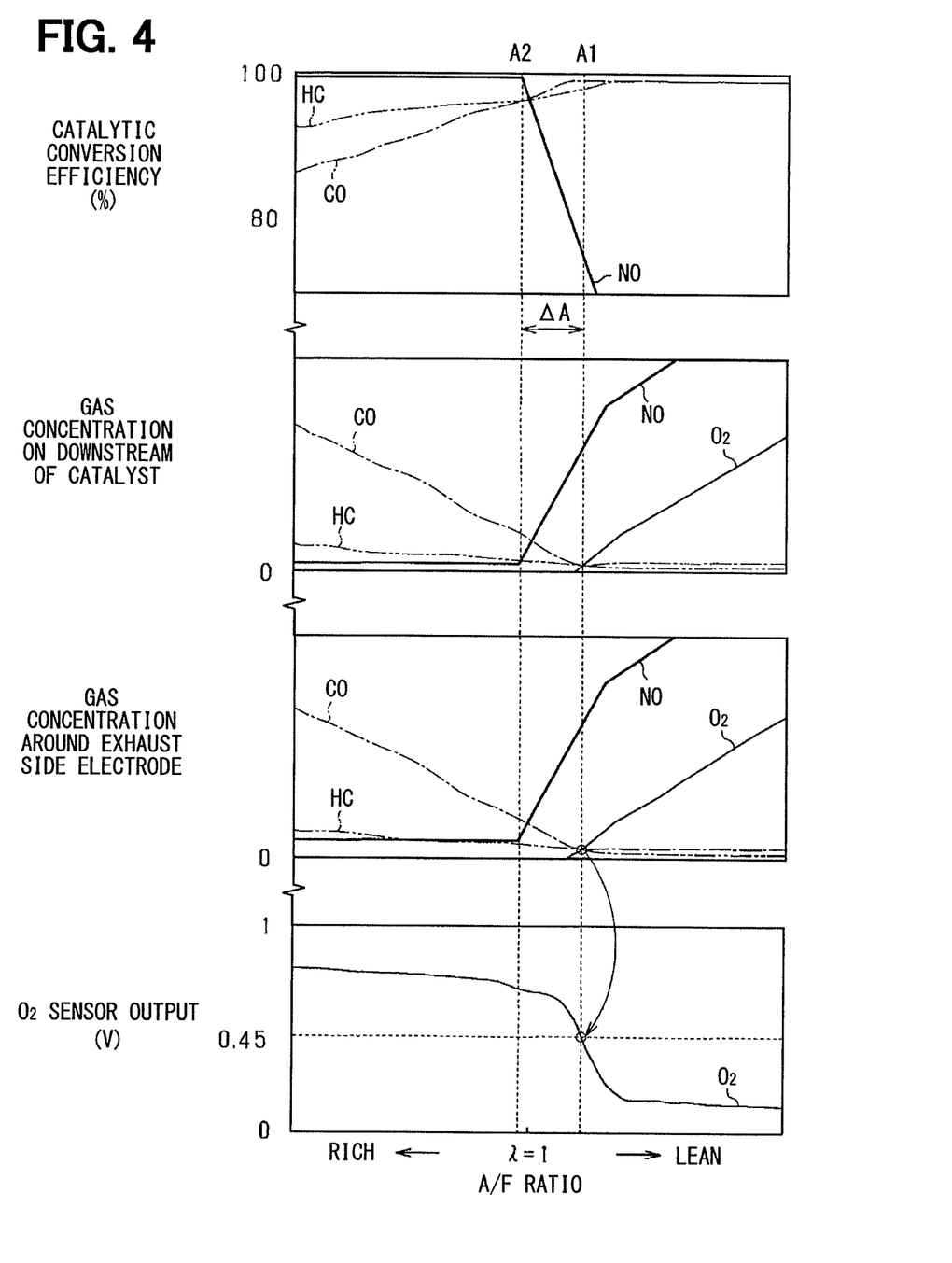
FIG. 4 is a diagram showing a catalytic conversion efficiency of a first catalyst and output characteristics of an $O_2$ sensor.

In the present embodiment, a sensing mode of the $O_2$ sensor 17 is changed based on the relationship between the output characteristic of the $O_2$ sensor 17, which outputs the electromotive force, and the exhaust gas purifying characteristic of the first catalyst 15a, which is placed on the upstream side of the $O_2$ sensor 17. Details of the change of the sensing mode of the $O_2$ sensor 17 will be described later. FIG. 4 is a diagram that shows the catalytic conversion characteristics of the first catalyst 15a, which is the three-way catalyst, and the output characteristics of the $O_2$ sensor 17. Specifically, FIG. 4 shows: (I) a relationship between a catalytic conversion efficiency of each of the three noxious components (i.e., CO, HC, NOx) of the exhaust gas at the first catalyst 15a and the air-to-fuel ratio; (II) a relationship between the gas concentration of each of the three noxious components and the oxygen on the downstream side of the first catalyst 15a and the air-to-fuel ratio; (III) a relationship between the gas concentration of each of the three noxious components and the oxygen around the surface of the exhaust side electrode 33 of the $O_2$ sensor 17 and the air-to-fuel ratio; and (IV) a relationship between the electromotive force output of the $O_2$ sensor 17 and the air-to-fuel ratio.

The first catalyst (the three-way catalyst) 15a has a catalytic conversion window, in which the catalytic conversion efficiency of each of the three noxious components becomes high around the point of the stoichiometric air-to-fuel ratio (percentage of excess air $\lambda=1$), as is known in the art. Furthermore, with respect to the concentrations of the three noxious components and the concentration of the oxygen on the downstream side of the first catalyst 15a, it is understood that a reaction equilibrium point A1, at which the concentrations of the rich components (CO, HC) and the concentration of the oxygen become generally equal to one another, is present around the point of the stoichiometric air-to-fuel ratio, and an NOx outflow point A2, at which the NOx (NO) begins to outflow from the first catalyst 15a on the downstream side of the first catalyst 15a, is also present. In this case, the NOx outflow point A2 (the point of starting the outflow of the NOx from the catalyst 15a) is located on the rich side of the reaction equilibrium point A1, and the NOx outflow point A2 and the reaction equilibrium point A1 are spaced from each other by a difference ΔA. That is, the first catalyst 15a has the catalytic conversion characteristic of that the NOx outflow point (serving as a second air-to-fuel ratio point) A2, at which the NOx begins to outflow from the first catalyst 15a, is located on the rich side of the reaction equilibrium point (serving as a first air-to-fuel ratio point) A1, which forms the equilibrium point for the rich components and the oxygen. The reaction equilibrium point A1 is an inflection point of the equilibrium characteristic of the rich components and the oxygen, and the NOx outflow point A2 is an inflection point of the outflow concentration characteristic of NOx.

The reason for the generation of the deviation (difference) between the point A1 and the point A2 may be as follows. In the case where the exhaust gas, which contains CO, HC, NOx, and $O_2$, is guided to the first catalyst 15a during the operation of the engine 10, NOx may possibly outflow from the first catalyst 15a in addition to CO and HC. For example, even in the range of the catalytic conversion window of the three-way catalyst, it will be noted that some amount of CO, HC, and NOx outflows from the first catalyst 15a when the amount of CO, HC, and NOx is precisely measured. In such a case, although $O_2$ outflows from the first catalyst 15a in equilibrium with CO and HC (starting of the outflow of $O_2$ at the concentration of CO and HC 0), NOx outflows from the first catalyst 15a on the downstream side thereof regardless of the reaction of CO and HC. Therefore, the difference exists between the point A1 and the point A2.

Furthermore, the concentrations of the above three components and the oxygen around the exhaust side electrode 33 of the $O_2$ sensor 17 are the same as the concentrations of the above three components and the oxygen on the downstream side of the first catalyst 15a. In this case, the amount of the rich components (CO, HC) is larger than the amount of oxygen on the rich side of the point A1, and the amount of oxygen is larger than the amount of the rich components on the lean side of the point A1. Therefore, in terms of the electromotive force of the $O_2$ sensor 17, one of a rich signal (0.9V) and a lean signal (0V) is outputted on one side or the other side of the reaction equilibrium point A1 of the first catalyst 15a. In this case, it can be said that the reaction equilibrium point for the rich components and the oxygen at the $O_2$ sensor 17 coincides with the reaction equilibrium point A1 at the first catalyst 15a. Furthermore, NOx is present on the rich side of the point A1.

At the exhaust side electrode 33 of the $O_2$ sensor 17, the oxidation reaction and the reduction reaction of CO, HC and NOx of the exhaust gas take place according to the following chemical reaction formulae (1) to (3).

$$CO + 0.5O_2 \rightarrow CO_2 \qquad (1)$$

$$CH_4 + 2O_2 \rightarrow CO_2 + 2H_2O \qquad (2)$$

$$CO + NO \rightarrow CO_2 + 0.5N_2 \qquad (3)$$

Furthermore, there is established a relationship of k1, k2>>K3 where k1, k2 and k3 denote an equilibrium constant of the chemical reaction formula (1), an equilibrium constant of the chemical reaction formula (2), and an equilibrium constant of the chemical reaction formula (3), respectively.

In this case, at the $O_2$ sensor 17, the equilibrium point (the point at which the electromotive force output=0.45 V) is determined through the gas reactions of, for example, CO, HC NOx, and $O_2$. However, due to the differences in the equilibrium constant, the reactions of CO and HC with $O_2$ become main reactions at the exhaust side electrode 33.

Furthermore, the above difference ΔA is present in the catalytic conversion characteristic of the first catalyst 15a, and the above difference ΔA has the influence on the output characteristic of the $O_2$ sensor 17. Therefore, even when NOx outflows from the first catalyst 15a, the output of the $O_2$ sensor 17 does not correspond to the outflow of NOx from the first catalyst 15a. Thus, the outflow of NOx from the first catalyst 15a cannot be correctly monitored, and thereby the amount of NOx emissions may possibly be increased.

Figure 5:
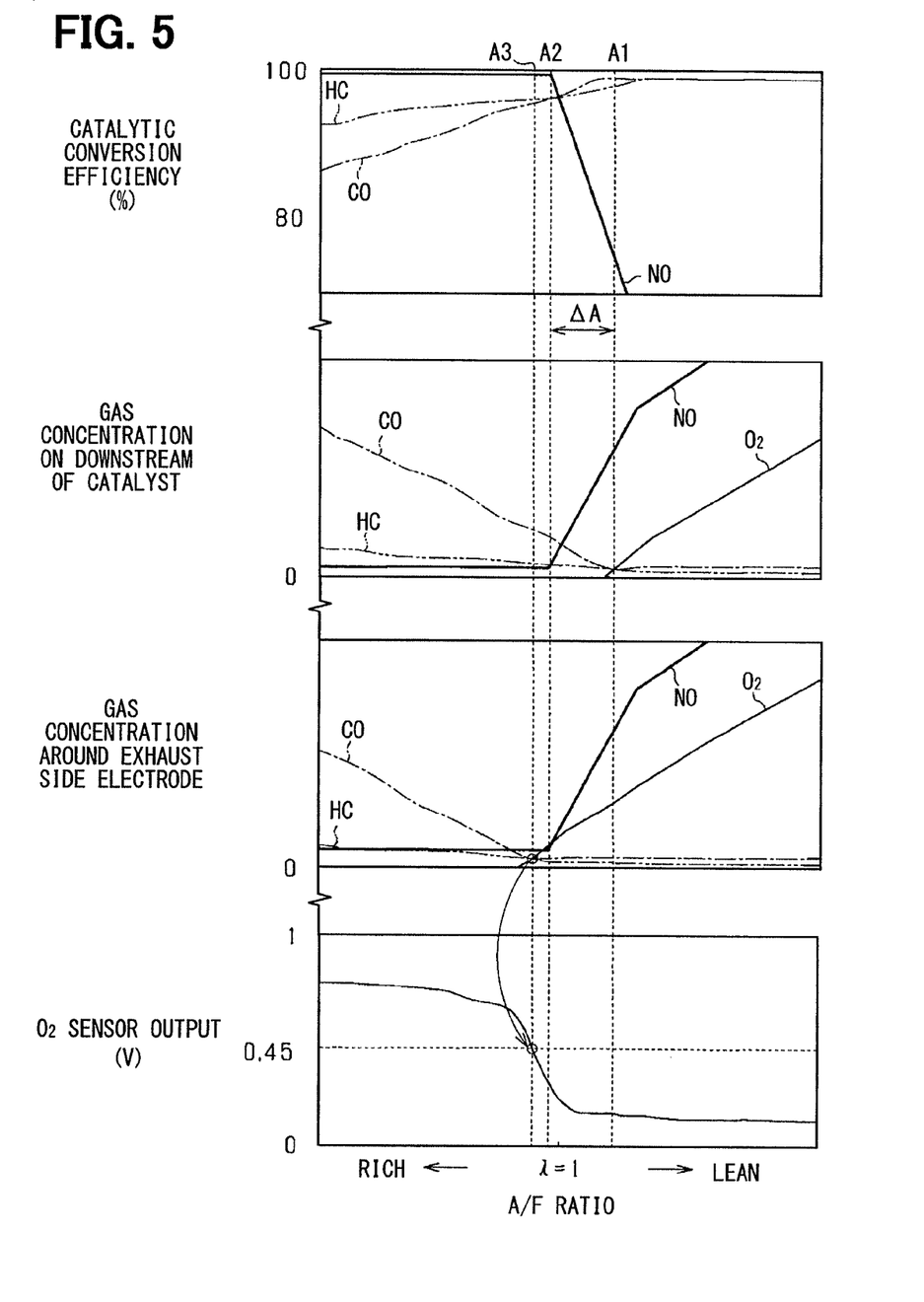
FIG. 5 is a diagram showing a catalytic conversion efficiency of a first catalyst and output characteristics of an $O_2$ sensor.

In view of the above disadvantage, according to the present embodiment, the electric current, which has a predetermined current value, is conducted between the electrodes 33, 34 of the sensor element 31 of the $O_2$ sensor 17, so that at the location around the exhaust side electrode 33 of the $O_2$ sensor 17, the concentrations of the rich components are reduced, and the concentration of the oxygen is increased. Specifically, as shown in FIG. 5, the equilibrium point of the gas reaction around the exhaust side electrode 33 of the $O_2$ sensor 17 is changed from the point A1 to a point A3. In FIG. 5, in comparison to FIG. 4, all of the concentration characteristics of CO, HC and $O_2$ around the exhaust side electrode 33 of the $O_2$ sensor 17 are shifted to the rich side. In this way, in the case where the output characteristic of the $O_2$ sensor 17 is changed, and NOx outflows from the first catalyst 15a, the output of the $O_2$ sensor 17 can correspond to the outflow of NOx.

Figure 6:
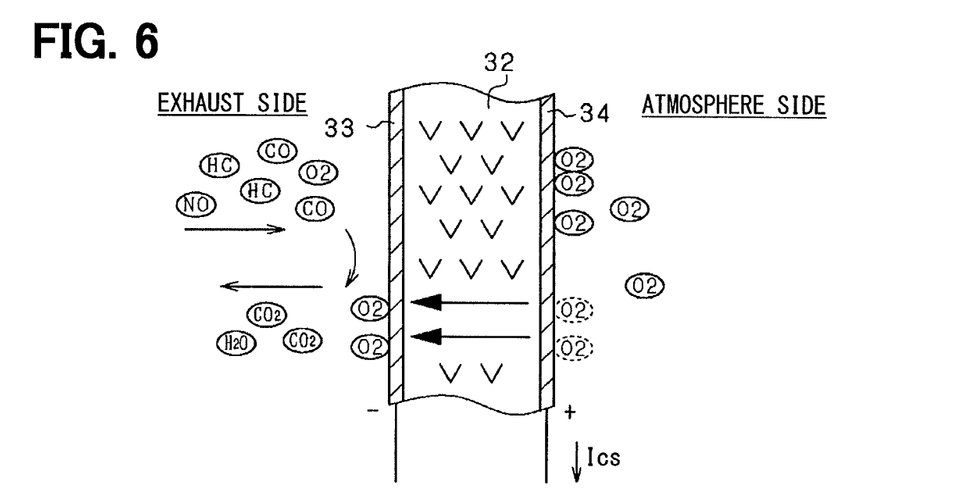
FIG. 6 is a schematic diagram for describing reactions of gas components at the sensor element.

The principle of inducing the change in the sensor output characteristic through conduction of the electric current between the electrodes 33, 34 is as follows. As shown in FIG. 6, CO, HC, NOx and $O_2$ are present around the exhaust side electrode 33 of the $O_2$ sensor 17. Under such a circumstance, the electric current is conducted through the sensor element 31 such that the oxygen ions are moved from the atmosphere side electrode 34 to the exhaust side electrode 33 through the solid electrolyte layer 32. Specifically, the oxygen pumping is executed at the sensor element 31. In this case, at the exhaust side electrode 33, the oxygen, which is moved to the exhaust side electrode 33 side through the solid electrolyte layer 32, reacts with CO and HC to form $CO_2$ and $H_2O$, respectively. In this way, CO and HC are removed around the exhaust side electrode 33, and the equilibrium point of the gas reaction around the exhaust side electrode 33 of the $O_2$ sensor 17 is shifted to the rich side.

Next, the structure of the sensor control arrangement 40, which executes the control operation with respect to the $O_2$ sensor 17, will be described. The structure of the sensor control arrangement 40 is one shown in FIG. 2. That is, the sensor control arrangement 40 includes the microcomputer 41, which serves as a control device (or control means). The microcomputer 41 obtains the electromotive force signal, which is outputted from the sensor element 31, through, for example, an analog-to-digital (A/D) converter and computes the air-to-fuel ratio (particularly, the air-to-fuel ratio on the downstream side of the first catalyst 15a) of the exhaust gas based on the obtained electromotive force signal. Furthermore, a constant current circuit (serving as a current conduction regulating device or current conduction regulating means) 43 is connected to a portion 50a1 of an electric path 50a that electrically connects between the atmosphere side electrode 34 of the sensor element 31 and the microcomputer 41. The portion 50a1 of the electric path 50a is an intermediate location between the atmosphere side electrode 34 of the sensor element 31 and the microcomputer 41 in the electric path 50a. The constant current circuit 43 is configured such that when the sensor element 31 generates the electromotive force, the constant current circuit 43 induces a flow of an electric current, which corresponds to the electromotive force of the sensor element 31, through the sensor element 31. In this case, the constant current circuit 43 induces the flow of the electric current from the exhaust side electrode 33 to the atmosphere side electrode 34 through the solid electrolyte layer 32, so that the oxygen ions move from the atmosphere side electrode 34 to the exhaust side electrode 33 through the solid electrolyte layer 32 in the sensor element 31.

In the present embodiment, the control of the constant electric current is executed based on a difference between the reaction equilibrium point A1 of the oxygen outflow at the first catalyst 15a and the NOx outflow point A2 of the NOx outflow at the first catalyst 15a. Particularly, the constant electric current is controlled such that the equilibrium point of the gas reaction around the exhaust side electrode 33 of the $O_2$ sensor 17 is placed at the NOx outflow point A2 or a point adjacent to the NOx outflow point A2. In this way, the output characteristic of the $O_2$ sensor 17 is changed based on the catalytic conversion efficiency of the first catalyst 15a. Thereby, when NOx outflows from the first catalyst 15a, the lean signal is outputted at the $O_2$ sensor 17 from the beginning of the outflow of NOx from the first catalyst 15a.

Here, in view of ensuring the robustness of the $O_2$ sensor 17 for the purpose of limiting the NOx emissions, it is desirable that the equilibrium point of the gas reaction around the exhaust side electrode 33 of the $O_2$ sensor 17 is placed on the rich side of the NOx outflow point A2 (see FIG. 5). Specifically, the equilibrium point of the gas reaction around the exhaust side electrode of the $O_2$ sensor 17 may be shifted from the NOx outflow point A2 on the rich side of the NOx outflow point A2 by the amount of, for example, about 0.1 to 0.5% (more desirably 0.1 to 0.3%) in terms of the percentage of excess air λ to have a slightly rich state.

The constant current circuit 43 of the sensor control arrangement 40 and a peripheral circuit thereof will be described in detail with reference to FIG. 7.

Figure 7:
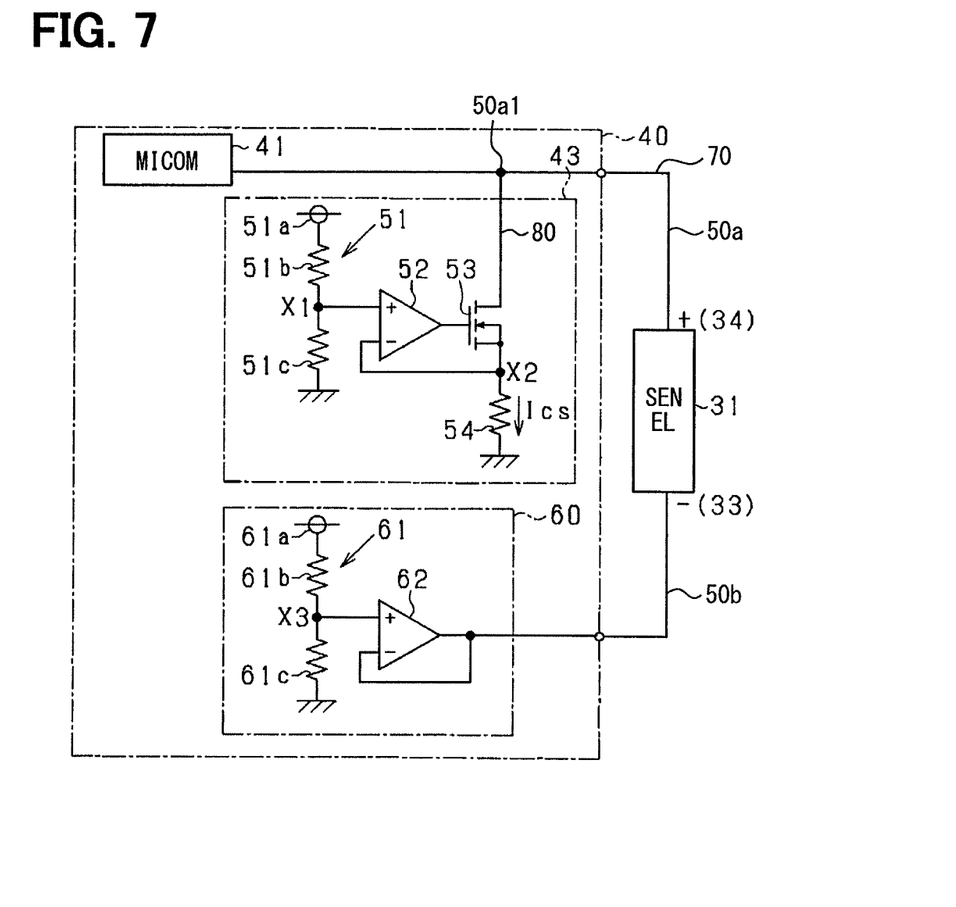
FIG. 7 is a diagram showing a structure of the sensor control arrangement.

With reference to FIG. 7, the constant current circuit 43 includes a voltage generating arrangement 51, an operational amplifier 52, an n-channel MOSFET 53 and a resistor 54. The operational amplifier 52 and the MOSFET 53 cooperate together to serve as an operating device. The voltage generating arrangement 51 generates a predetermined constant voltage. The MOSFET 53 and the resistor 54 are connected in series in an electric path 80, which connects between the portion 50a1 of the electric path 50a and a ground. The electric path 50a and the electric path 80 cooperate together to form an electric path 70 that connects between the atmosphere side electrode 34 of the $O_2$ sensor 17 and the ground (earth). The n-channel MOSFET 53 is driven by an output of the operational amplifier 52. The resistor 54 is connected to a source of the MOSFET 53. The voltage generating arrangement 51 includes a constant voltage source 51a (e.g., a constant voltage source that outputs 5V) and two resistors 51b, 51c. The constant voltage source 51a and the resistors 51b, 51c are connected in series, and an intermediate point between the resistors 51b, 51c forms a voltage output point X1. A non-inverting terminal (also referred to as a + input terminal) of the operational amplifier 52 is connected to the voltage output point X1 and an output terminal of the operational amplifier 52 is connected to a gate of the MOSFET 53. Furthermore, an inverting terminal (also referred to as a − input terminal) of the operational amplifier 52 is connected to an intermediate point X2 between the MOSFET 53 and the resistor 54 in the electric path 80. The gate, the drain and the source of the MOSFET 53 are connected to the output terminal of the operational amplifier 52, the atmosphere side electrode 34 of the sensor element 31 and the resistor 54, respectively.

The constant current circuit 43, which is constructed in the above-described manner, is operated such that the voltage of the non-inverting terminal of the operational amplifier 52 and the voltage of the inverting terminal of the operational amplifier 52 become equal to each other. Therefore, the voltage of the intermediate point X2 and the voltage of the voltage output point X1 are equal to each other. A constant electric current Ics, which has a current value determined based on the voltage of the intermediate point X2 and the resistance value of the resistor 54, flows through a series circuit that is formed in the electric path 70 and includes the sensor element 31, the MOSFET 53 and the resistor 54 that are connected one after another in series. At this time, the MOSFET 53 is operated in response to an output voltage of the operational amplifier 52, which is generated due to a difference between the input voltage of the non-inverting terminal and the input voltage of the inverting terminal of the operational amplifier 52, so that the MOSFET 53 functions as a current control element that conducts the constant electric current Ics. The voltage of the intermediate point X2 serves as a reference voltage.

Desirably, the voltage of the voltage output point X1, the voltage of the intermediate point X2 and the resistance value of the resistor 54 are determined based on the current value of the electric current that needs to be conducted through the sensor element 31 at the time of generating the electromotive force in the sensor element 31. Specifically, for instance, in a case where the electric current, which has the current value of 0.1 mA, needs to be conducted through the sensor element 31 at the time of generating the electromotive force (0 to 0.9V) in the sensor element 31, the voltage of the voltage output point X1 and the voltage of the intermediate point X2 are set to be 10 mV, and the resistance value of the resistor 54 is set to be 100Ω. Furthermore, in a case where the electric current, which has the current value of 0.2 mA, needs to be conducted through the sensor element 31, the voltage of the voltage output point X1 and the voltage of the intermediate point X2 are set to be 20 mV, and the resistance value of the resistor 54 is set to be 100Ω. In addition, in a case where the electric current, which has the current value in a range of 0.1 mA to 1.0 mA, needs to be conducted through the sensor element 31, the voltage of the voltage output point X1 and the voltage of the intermediate point X2 are set to be in a range of 10 mV to 100 mV, and the resistance value of the resistor 54 is set to be 100Ω. However, in such a case, the reference voltage, which is the voltage of the intermediate point X2 between the MOSFET 53 and the resistor 54 in the constant current circuit 43, is smaller than the electromotive force (0.45 V) of the sensor element 31 generated at the stoichiometric air-to-fuel ratio.

Desirably, the range of the resistance value of the resistor 54 is about 50Ω to 500Ω. Here, it is assumed that the resistance value of the sensor element 31 is 350Ω, and the current value of the electric current, which flows through the sensor element 31, is 1.0 mA. Also, it is assumed that the resistance value of the resistor 54 is 500Ω. In such a case, when the electromotive force is equal to or larger than 0.85 V, the electric current, which has the desirable current value (1.0 mA), can be conducted through the sensor element 31. In view of the electromotive force of the sensor element 31 in the rich state, the electric current, which has the desirable current value (1.0 mA), can be conducted through the sensor element 31 in the case where the resistance value of the resistor 54 is 500Ω. This resistance value of the resistor 54 is defined as a maximum resistance value of the resistor 54. Furthermore, in order to enable the conduction of the electric current, which has the desirable current value (1.0 mA), through the sensor element 31 in the state of the stoichiometric air-to-fuel ratio, the maximum resistance value of the resistor 54 is desirably set to 100Ω. However, the resistance value of the resistor 54 is not limited to the above value in a case where the maximum resistance value of the sensor element 31 in the activated state of the sensor element 31 is set to be equal to or smaller than 350Ω. For example, in a case where the maximum resistance value of the sensor element 31 in the activated state is set to be 300Ω, the maximum resistance value of the resistor 54 may be set to 150Ω. The minimum resistance value (50Ω) of the resistor 54 is set to enable sensing of an abnormality. In such a case, when the resistance value of the resistor 54 is 50Ω, the voltage of the sensor element 31 becomes 5 mV at the time of conducting the electric current having the current value of 0.1 mA through the sensor element 31. In such a case, when a 14-bit A/D converter having a voltage range of 0 to 5 V is used, a measurement value will be 16 (2^14/1000). Therefore, the abnormality can be appropriately sensed.

In the sensor control arrangement 40, which has the constant current circuit 43 of the above structure, when the electromotive force is generated in the sensor element 31, the predetermined constant electric current Ics is conducted through the MOSFET 53 and the resistor 54 while using the electromotive force of the sensor element 31 as an electric power source (in other words, the sensor element 31 being used as a battery). Thereby, the output characteristic of the $O_2$ sensor 17 can be changed.

Figure 8:
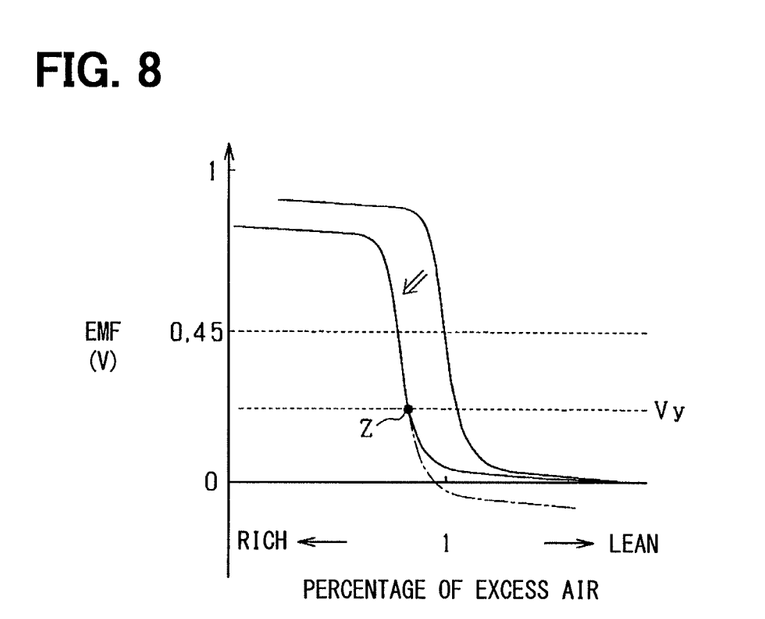
FIG. 8 is an electromotive force characteristic diagram indicating a relationship between an air-to-fuel ratio and an electromotive force of the sensor element.

FIG. 8 is a diagram for describing the output characteristic of the sensor element 31 in the case where the constant electric current Ics is conducted in the sensor element 31 through use of the constant current circuit 43. In FIG. 8, a characteristic line, which indicates the output characteristic of the sensor element 31, is shifted to the rich side as indicated by an arrow when the constant electric current Ics is conducted through the MOSFET 53 and the resistor 54 to conduct the constant electric current ICs through the sensor element 31. Furthermore, in the circuit structure shown in FIG. 7, the electromotive force of the sensor element 31 is sensed at an intermediate point between the sensor element 31 and the MOSFET 53 in the series circuit, which includes the sensor element 31, the MOSFET 53 and the resistor 54 in the electric path 70, so that the electromotive force of the sensor element 31 becomes relatively small.

Here, in the case where the constant electric current Ics is conducted through the sensor element 31, it is desirable that the current value of the constant electric current Ics is kept constant to implement movement of the constant amount of the oxygen ions in the sensor element 31 even when the electromotive force of the sensor element 31 is changed in the range of 0 to 0.9 V. However, in the case where the constant current circuit 43 of the above structure is used, the flow of the constant electric current Ics is generated while using the electromotive force of the sensor element 31 as the electric power source. Therefore, in a range where the electromotive force of the sensor element 31 is relatively small, the current value of the constant electric current Ics becomes relatively small. Specifically, in a range where the electromotive force is equal to or larger than a lower threshold voltage Vy in FIG. 8, the constant current value of the constant electric current Ics can be maintained. In contrast, in a range where the electromotive force is smaller than the lower threshold voltage Vy, the constant current value of the constant electric current Ics cannot be maintained and thereby becomes smaller than a proper value. With reference to the output characteristic of the sensor element 31 of FIG. 8, the output characteristic becomes one indicated by a dotted line on a lower voltage side, which is lower than a point Z in FIG. 8, in the case where the constant current value of the constant electric current Ics is provided to shift the output characteristic of the sensor element 31 throughout the entire electromotive force range of the sensor element 31. However, when the current value is reduced in the range where the electromotive force of the sensor element 31 becomes smaller than the lower threshold voltage Vy, the amount of shift of the output characteristic is reduced on the lower voltage side of the point Z as indicated by a solid line in FIG. 8. The lower threshold voltage Vy is a threshold voltage, above which the appropriate flow of the constant current Ics in the constant current circuit 43 is guaranteed. In the structure of FIG. 7, the lower threshold value Vy is set to be a voltage that corresponds to the voltage of the intermediate point X2 and an on-state resistance of the MOSFET 53 (a voltage drop at the time of turning on of the MOSFET 53).

Figure 9A:
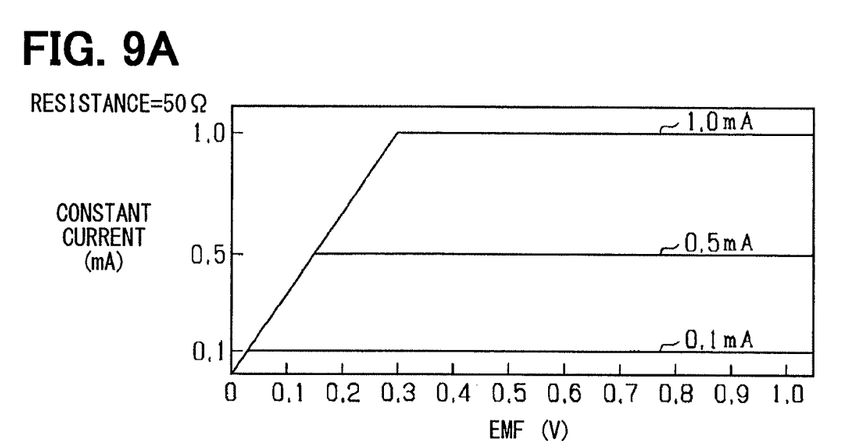
FIGS. 9A to 9C are diagrams for describing a relationship between the electromotive force of the sensor element and a constant electric current.
Figure 9B:
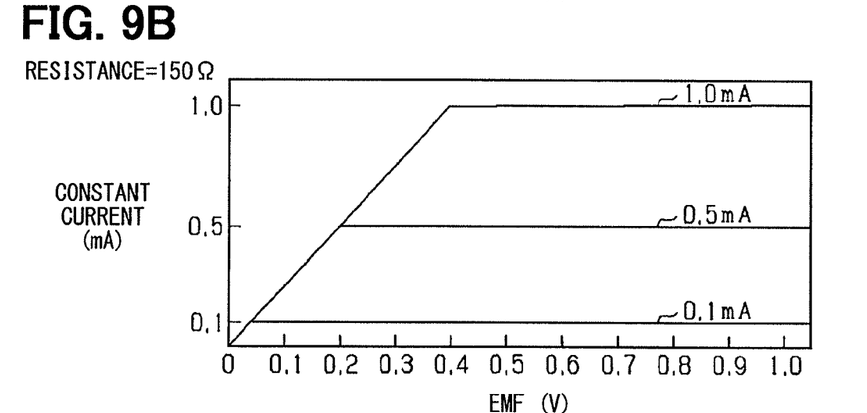
Figure 9C:
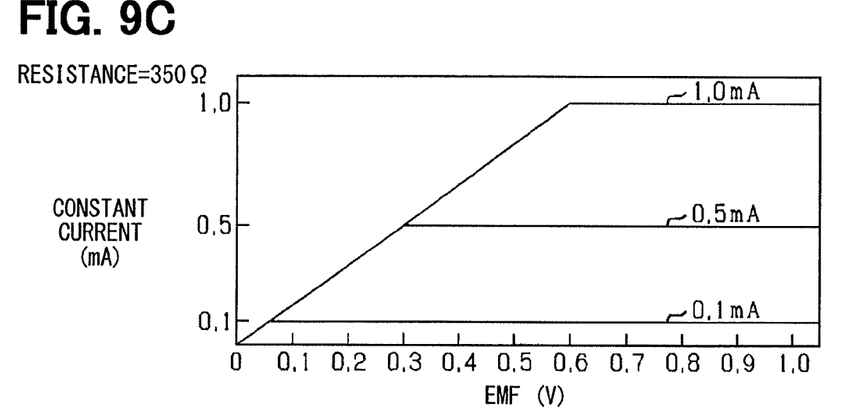

The lower threshold voltage Vy varies depending on the resistance value of the sensor element 31, which indicates the activated state of the sensor element 31, and/or the current value of the constant electric current Ics that needs to be conducted through the sensor element 31 through use of the constant current circuit 43. FIGS. 9A to 9C indicate this relationship. FIG. 9A indicates a case where the resistance value of the sensor element 31 is 50Ω. FIG. 9B indicates a case where the resistance value of the sensor element 31 is 150Ω. FIG. 9C indicates a case where the resistance value of the sensor element 31 is 350Ω.

With reference to FIGS. 9A to 9C, it would be understood that the threshold voltage Vy (i.e., the electromotive force of the sensor element 31 that enables the flow of the electric current having the proper current value) is increased when the current value of the constant electric current Ics is increased. For example, in FIG. 9A, in the case where the current value of the constant electric current Ics is 0.1 mA, the lower threshold voltage Vy is 0.03 V. Also, in FIG. 9A, in the case where the current value of the constant electric current Ics is 0.5 mA, the lower threshold voltage Vy is 0.15 V. Furthermore, in FIG. 9A, in a case where the current value of the constant electric current Ics is 1.0 mA, the lower threshold voltage Vy is 0.3 V. Furthermore, in FIG. 9B, in a case where the current value of the constant electric current Ics is 0.1 mA, the lower threshold voltage Vy is 0.04 V. Also, in FIG. 9B, in a case where the current value of the constant electric current Ics is 0.5 mA, the lower threshold voltage Vy is 0.2 V. Furthermore, in FIG. 9B, in a case where the current value of the constant electric current Ics is 1.0 mA, the lower threshold voltage Vy is 0.4 V. Furthermore, in FIG. 9C, in the case where the current value of the constant electric current is 0.1 mA, the lower threshold voltage Vy is 0.06 V. Also, in FIG. 9C, in the case where the current value of the constant electric current is 0.5 mA, the lower threshold voltage Vy is 0.3 V. Furthermore, in FIG. 9C, in the case where the current value of the constant electric current is 1.0 mA, the lower threshold voltage Vy is 0.6 V. The constant current circuit 43 of the present embodiment enables the flow of the constant electric current through the sensor element 31 at the time of outputting the electromotive force in the rich state. Furthermore, desirably, the constant current circuit 43 of the present embodiment enables the flow of the required constant electric current in an electromotive force range, which is equal to or larger than the electromotive force (0.45 V) of the sensor element 31 generated at the stoichiometric air-to-fuel ratio. In such a case, although the lower threshold voltage Vy is 0.6 V (in the case where the current value of the constant electric current is 1.0 mA) in FIG. 9C, for instance, an upper limit of the range of the current value of the constant electric current may be reduced to meet this demand.

In this case, the movement of the oxygen ions from the atmosphere side electrode 34 to the exhaust side electrode 33 may possibly be unintentionally reduced or stopped only in the small electromotive force range (the range that is smaller than the lower threshold voltage Vy in FIG. 8) of the sensor element 31. In such a case, when the electromotive force of the sensor element 31 is changed in response to a change in the air-to-fuel ratio of the exhaust gas, the movement of the oxygen ions may be an expected movement in some cases or an unexpected movement in some other cases. Thereby, the output characteristic of the $O_2$ sensor 17 may possibly be influenced throughout the entire electromotive force output range of the $O_2$ sensor 17.

In view of the above point, according to the present embodiment, as shown in FIGS. 2 and 7, a voltage circuit 60 is installed in the electric path 50b, which connects between the exhaust side electrode 33 of the sensor element 31 and the ground, to apply a positive voltage from the voltage circuit 60 to the exhaust side electrode 33. The voltage circuit 60 is an offset voltage circuit that raises, i.e., increases an electric potential of the exhaust side electrode 33 by a predetermined amount (predetermined electric potential) relative to an electric potential of the output side of the constant current circuit 43, from which the electric current flows out of the constant current circuit 43 (i.e., an electric potential on the ground side of the resistor 54 where the ground is located). The voltage circuit 60 includes a voltage generating arrangement 61 and a buffer circuit 62. The voltage generating arrangement 61 generates a predetermined offset voltage. The buffer circuit 62 is made of an operational amplifier. The voltage generating arrangement 61 includes a constant voltage source 61a (e.g., a constant voltage source that outputs 5V) and two resistors 61b, 61c. The constant voltage source 61a and the resistors 61b, 61c are connected in series, and an intermediate point between the resistors 61b, 61c forms an offset voltage point X3. The offset voltage point X3 is connected to the buffer circuit 62, and an output voltage of the buffer circuit 62 is maintained at the voltage (voltage value) that is the same as the voltage (voltage value) of the offset voltage point X3. The voltage (voltage value) of the offset voltage point X3 is, for example, 2.0 V.

With the above-described structure, which has the voltage circuit 60, even in the small electromotive force range, in which the electromotive force of the sensor element 31 is relatively small, the current value of the constant electric current, which is induced by the constant current circuit 43 and flows between the exhaust side electrode 33 and the atmosphere side electrode 34, can be kept to the required level (i.e., can be limited from falling to the excessively low level). That is, it is possible to limit the excessive reduction of the current value of the electric current, which is induced by the constant current circuit 43 and is conducted through the sensor element 31. Thus, it is possible to limit the undesirable reduction in the amount of shift, which is indicated by the solid line in FIG. 8, on the lower voltage side of the point Z in FIG. 8.

Although the microcomputer 41 receives a voltage signal (input voltage), which is a sum of the electromotive force of the sensor element 31 and the offset voltage, the voltage value of the offset voltage is known at the microcomputer 41. Therefore, the microcomputer 41 can sense the air-to-fuel ratio based on a value, which is obtained by subtracting the voltage value of the offset voltage from the voltage value of the input voltage, which is inputted to the microcomputer 41.

Figure 10:
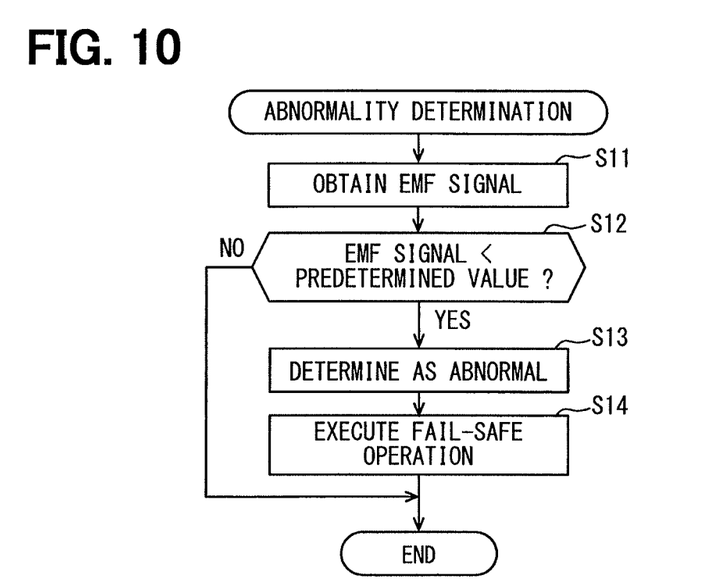
FIG. 10 is a flowchart showing a breaking abnormality determination process.

Furthermore, with the above-described structure, in which the voltage circuit 60 is connected, the electromotive force signal, in which the offset voltage is added, is outputted to the microcomputer 41. Therefore, the voltage value of the electromotive force signal is always equal to or larger than the voltage value of the offset voltage regardless of the voltage value of the sensor element 31, which is in the range of 0 to 0.9 V. In the present embodiment, a breaking abnormality determination for determining whether breaking of the conductive line is present is executed based on this fact. FIG. 10 shows the flowchart indicating the breaking abnormality determination process. This process is repeated at predetermined time intervals by the microcomputer 41.

In FIG. 10, at step S11, the electromotive force signal is obtained. Then, at step S12, it is determined whether a voltage value of the obtained electromotive force signal is less than a predetermined value. This predetermined value may be, for instance, the same as the voltage value of the offset voltage of the voltage circuit 60. Alternatively, the predetermined value may be slightly smaller than the voltage value of the offset voltage of the voltage circuit 60. When the answer to the inquiry at step S12 is YES, the operation proceeds to step S13. At step S13, it is determined that the breaking abnormality (the breaking of the conductive line) is present in the electric path 70 connected to the sensor element 31. Thereafter, at step S14, there is executed a fail-safe operation, such as stopping of the conduction of the electric current through the constant current circuit 43, stopping of the sub-feedback control operation of the air-to-fuel ratio, turning on of an abnormality warning lamp provided in, for example, an instrument panel, and/or storing of diagnosis data in a storage device (e.g., a memory).

The microcomputer 41 includes a voltage signal obtaining section, and an abnormality determining section to execute the breaking abnormality determination process of FIG. 10. Specifically, the voltage signal obtaining section obtains the voltage signal of the electromotive force, which is outputted from the sensor element 31, as discussed above with reference to step S11. The abnormality determining section determines whether the breaking abnormality is present in the electric path 70, which is connected to the sensor element 31, based on the voltage signal of the electromotive force, as discussed above with reference to step S S12 and S13. Each of the voltage signal obtaining section, and the abnormality determining section may be implemented by a corresponding program that is stored in the memory and is executed by the CPU in the microcomputer 41. Furthermore, these sections may be implemented by more than one microcomputer, if desired.

The present embodiment discussed above provides the following advantages.

The sensor element 31 can be used as the battery by using the electromotive force of the sensor element 31. In view of this point, the constant current circuit (serving as the current conduction regulating device or the current conduction regulating means) 43 is formed as the circuit that conducts the electric current while using the electromotive force generated at the sensor element 31 as the electric power source of the electric current. In this case, when the sensor element 31 is used as the battery, it is not required to provide another electric power source, which is used as a substitution of the sensor element 31. Therefore, the structure of the constant current circuit 43 can be simplified. With this simplification of the structure, the cost reduction is possible.

On the other hand, the electromotive force of the sensor element 31 changes in the range of, for example, 0 to 0.9 V. In the case where the sensor element 31 is used as the battery, when the electromotive force becomes small, the current value of the electric current, which is induced by the constant current circuit 43 and is conducted through the sensor element 31, may possibly become excessively small. In view of this point, there is provided the voltage circuit 60 that raises the electric potential of the exhaust side electrode 33 by the predetermined amount (predetermined electric potential) relative to the electric potential of the output side of the constant current circuit 43, from which the electric current flows out of the constant current circuit 43 (i.e., the electric potential on the ground side of the resistor 54 where the ground is located). Therefore, even in the relatively small electromotive force range, it is possible to limit the excessive reduction of the current value of the electric current, which is induced by the constant current circuit 43 and is conducted through the sensor element 31. Therefore, the structure is simplified, and the electric current, which has the desirable current value, can be conducted through the sensor element 31 regardless of the voltage value of the electromotive force generated at the sensor element 31. Thereby, the output characteristic of the $O_2$ sensor 17 can be appropriately changed.

The constant current circuit 43 is constructed to have the structure that enables the flow of the required constant electric current Ice having the constant current value in the electromotive force range, which is equal to or larger than the electromotive force (0.45 V) of the sensor element 31 generated at the stoichiometric air-to-fuel ratio. Specifically, with respect to the characteristic of FIG. 8, the required constant electric current Ics can be conducted through the sensor element 31 in the range that is equal to or larger than the point Z, which is smaller than the stoichiometric point. In this case, the output characteristic of the $O_2$ sensor 17 can be changed in the desirable manner in at least the range of the stoichiometric air-to-fuel ratio to the rich air-to-fuel ratio.

Through use of the constant current circuit 43, which is constructed in the above-described manner, the output characteristic of the $O_2$ sensor 17 can be adjusted to correspond with the air-to-fuel ratio at the point where the outflow of NOx begins at the first catalyst 15a. That is, in the case where NOx outflows from the first catalyst 15a, the $O_2$ sensor 17 can generate the corresponding electromotive force, which corresponds to the outflow of NOx from the first catalyst 15a. Therefore, the output characteristic of the $O_2$ sensor 17 can be appropriately changed, and thereby the NOx emissions can be limited.

The constant electric current Ics, which is conducted by the constant current circuit 43, shifts the equilibrium point of the gas reaction around the exhaust side electrode 33 of the $O_2$ sensor 17 to the NOx outflow point A2 (the second air-to-fuel ratio point) or the point adjacent to the NOx outflow point A2. Thereby, it is possible to implement the more appropriate structure for limiting the emissions of NOx through use of the output of the $O_2$ sensor 17.

Particularly, when the constant electric current Ics is supplied to the sensor element 31 through the constant current circuit 43 in such a manner that the equilibrium point of the gas reaction around the exhaust side electrode 33 of the $O_2$ sensor 17 becomes slightly rich relative to the NOx outflow point A2 (the second air-to-fuel ratio point), the required robustness can be achieved to limit the NOx emissions.

In the structure, which is configured to apply the positive voltage from the voltage circuit 60 to the exhaust side electrode 33, the occurrence of the breaking abnormality of the conductive line can be appropriately determined through the execution of the breaking sensing operation based on the electromotive force signal in the state where the positive voltage is applied from the voltage circuit 60 to the exhaust side electrode 33.

The present disclosure is not necessarily limited to the above embodiment, and the above embodiment may be modified in various ways within the principle of the present disclosure. For example, the above embodiment may be modified as follows.

Figure 11:
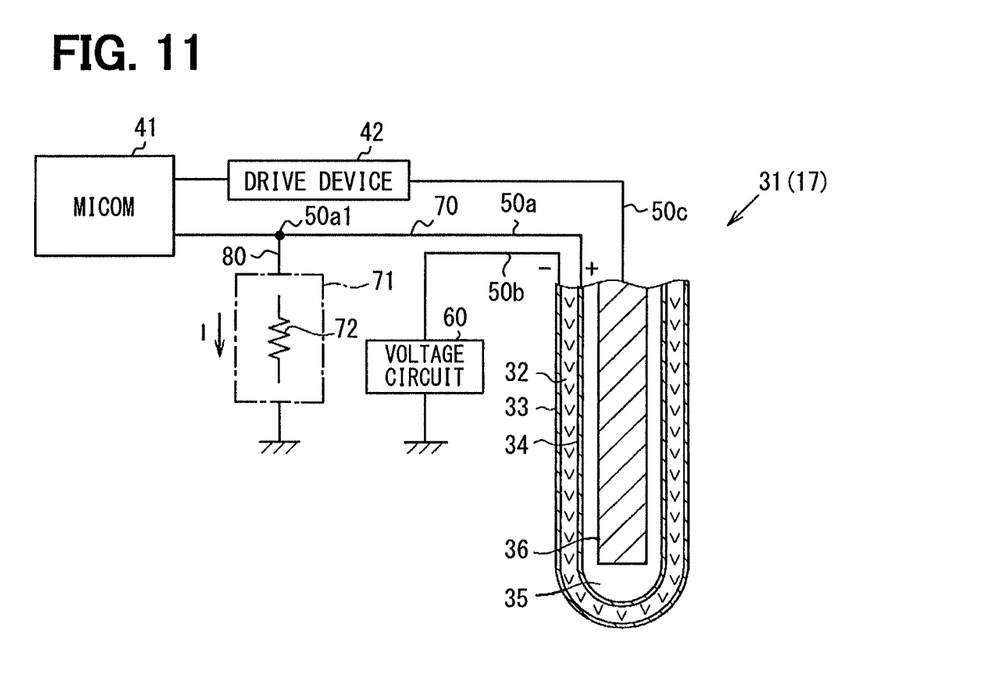
FIG. 11 is a diagram showing a structure of a sensor control arrangement in a modification of the embodiment.

The structure of the sensor control arrangement 40 may be changed. For instance, as shown in FIG. 11, in place of the constant current circuit 43 of the above embodiment, a resistor circuit (serving as a current conduction regulating device or current conduction regulating means) 71 may be installed in the electric path 80, which connects between the portion 50a1 of the electric path 50a and the ground. The resistor circuit 71 is configured to induce the flow of the electric current through the sensor element 31 when the sensor element 31 generates the electromotive force. The resistor circuit 71 is a current conducting circuit that conducts the electric current, which corresponds to the electromotive force of the sensor element 31, when the electromotive force of the sensor element 31 is applied to the resistor circuit 71. The resistor circuit 71 includes a resistor 72, which is installed in the electric path 80 that connects between the atmosphere side electrode 34 of the $O_2$ sensor 17 and the ground (earth), more specifically, between the portion 50a1 of the electric path 50a and the ground. The resistor 72 serves as a current conducting resistor. In this case, when an electric current I flows through the resistor 72 in the electric path 80 to the ground, the corresponding electric current flows from the exhaust side electrode 33 to the atmosphere side electrode 34 through the solid electrolyte layer 32 in the sensor element 31, and thereby the oxygen ions move from the atmosphere side electrode 34 to the exhaust side electrode 33 through the solid electrolyte layer 32 in the sensor element 31.

Even in this structure, the voltage circuit 60, which applies the positive voltage to the exhaust side electrode 33, is installed in the electric path 50 between the exhaust side electrode 33 and the ground. Therefore, it is possible to limit the excessive reduction of the current value of the electric current that flows through the resistor circuit 71 in the small electromotive force range, in which the electromotive force of the sensor element 31 becomes relatively small.

In the above embodiment, the $O_2$ sensor 17 is placed on the downstream side of the first catalyst 15a. Alternatively, the $O_2$ sensor 17 may be installed to an intermediate portion of the first catalyst 15a. In such a case, the $O_2$ sensor 17 may be installed to the substrate of the first catalyst 15a. In any of the above cases, it is only required that the $O_2$ sensor 17 is constructed to use the exhaust gas after the purification thereof at the first catalyst 15a as the sensing subject to sense the gas component(s).

Besides the $O_2$ sensor 17 having the above-described structure, the gas sensor may be a gas sensor that has a two-cell structure, which includes an electromotive force cell and a pump cell. In such a case, the output characteristic can be appropriately changed at the electromotive force cell of the two-cell type gas sensor.

What is claimed is:

1. A gas sensor control apparatus for use with a gas sensor installed in an exhaust device of an internal combustion engine, the gas sensor
    outputting an electromotive force signal corresponding to an air-to-fuel ratio of an exhaust gas of the internal combustion engine conducted through the exhaust device, and
    having an electromotive force cell,
        the electromotive force cell having a solid electrolyte body and a pair of electrodes, wherein the solid electrolyte body is held between the pair of electrodes,
        the pair of electrodes including
            a reference side electrode that becomes a positive side at a time of outputting an electromotive force from the electromotive force cell, and
            an exhaust side electrode that becomes a negative side at the time of outputting the electromotive force from the electromotive force cell, the gas sensor control apparatus comprising:
    a current conduction regulating device that is installed in an electric path that is connected to the electromotive force cell, the current conduction regulating device inducing a flow of an electric current between the exhaust side electrode and the reference side electrode through the solid electrolyte body in the electromotive force cell while using the electromotive force of the electromotive force cell as an electric power source; and
    a voltage circuit that increases an electric potential of the exhaust side electrode by a predetermined amount relative to an electric potential at an output side of the current conduction regulating device, from which the electric current flows out of the current conduction regulating device, wherein:
    the gas sensor control apparatus further comprises a control device programmed to control the current conduction regulating device;
    an exhaust gas purifying device is installed in the exhaust device of the internal combustion engine and includes a catalyst that purifies NOx, which is a lean component of the exhaust gas, and a rich component of the exhaust gas;
    the gas sensor is installed in the exhaust device at a location, which is in an intermediate portion of the catalyst or on a downstream side of the catalyst, to sense the air-to-fuel ratio of the exhaust gas after purification of the exhaust gas with the catalyst;
    the catalyst has a conversion characteristic, which indicates a relationship between the air-to-fuel ratio and a catalytic conversion efficiency of the catalyst;
    the conversion characteristic of the catalyst includes a second air-to-fuel ratio point, which is a point of starting an outflow of the NOx from the catalyst on the downstream side of the catalyst and is located on a rich side of a first air-to-fuel ratio point that is an equilibrium point for the rich component and oxygen, a concentration of the rich component and a concentration of the oxygen becoming generally equal to one another at the equilibrium point on the downstream side of the catalyst; and
    the control device controls the current conduction regulating device such that the current conduction regulating device induces the flow of the electric current that is conducted between the exhaust side electrode and the reference side electrode at a current value that corresponds to a difference between the first air-to-fuel ratio point and the second air-to-fuel ratio point.

2. The gas sensor control apparatus according to claim 1, wherein
    the current conduction regulating device induces the flow of the electric current, which is a constant electric current having a constant current value, in a corresponding electromotive force range, which is equal to or larger than a predetermined electromotive force of the electromotive force cell that is generated at a theoretical air-to-fuel ratio of the exhaust gas.

3. The gas sensor control apparatus according to claim 1, wherein
    the current conduction regulating device induces the flow of the electric current that is conducted between the exhaust side electrode and the reference side electrode and has the current value, which is required to shift an equilibrium point of a gas reaction around the exhaust side electrode of the electromotive force cell, to the second air-to-fuel ratio point or an adjacent point that is adjacent to the second air-to-fuel ratio point.

4. The gas sensor control apparatus according to claim 3, wherein
    the current conduction regulating device induces the flow of the electric current that is conducted between the exhaust side electrode and the reference side electrode and has the current value, which is required to shift the equilibrium point of the gas reaction around the exhaust side electrode of the electromotive force cell, to a rich side of the second air-to-fuel ratio point.

5. The gas sensor control apparatus according to claim 1, comprising:

a voltage signal obtaining section that obtains a voltage signal of the electromotive force, which is outputted from the electromotive force cell; and an abnormality determining section that determines whether a breaking abnormality is present in the electric path, which is connected to the electromotive force cell, based on the voltage signal of the electromotive force.

* * * * *